United States Patent [19]

Chandraratna

[11] Patent Number: 5,324,744

[45] Date of Patent: Jun. 28, 1994

[54] 7-CHROMANYL ESTERS OF PHENOLS AND BENZOIC ACIDS HAVING RETINOID-LIKE ACTIVITY

[75] Inventor: Roshantha A. S. Chandraratna, El Toro, Calif.

[73] Assignee: Allergan, Inc., Irvine, Calif.

[21] Appl. No.: 918,538

[22] Filed: Jul. 22, 1992

Related U.S. Application Data

[62] Division of Ser. No. 676,152, Mar. 26, 1991, Pat. No. 5,134,159.

[51] Int. Cl.$^5$ ............... A61K 31/35; C07D 311/04
[52] U.S. Cl. ............... 514/456; 549/410; 549/370; 549/347; 514/452; 514/450
[58] Field of Search ............... 514/456, 452, 450; 549/410, 405, 370, 347

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. . |
| 4,695,649 | 9/1987 | Magami et al. . |
| 4,723,028 | 2/1988 | Shudo . |
| 4,739,098 | 4/1988 | Chandraratna . |
| 4,740,519 | 4/1988 | Shroot et al. . |
| 4,810,804 | 3/1989 | Chandraratna . |
| 4,826,969 | 5/1989 | Maignan et al. . |
| 4,855,320 | 8/1989 | Chatterjee et al. . |
| 4,895,868 | 1/1990 | Chandraratna . |
| 4,980,369 | 12/1990 | Chandraratna . |
| 4,992,468 | 2/1991 | Chandraratna . |
| 5,006,550 | 4/1991 | Chandraratna . |

(List continued on next page.)

FOREIGN PATENT DOCUMENTS

| | | |
|---|---|---|
| 0130795 | 1/1985 | European Pat. Off. . |
| 176034A | 4/1986 | European Pat. Off. . |
| 0284288 | 9/1988 | European Pat. Off. . |
| 0350846 | 7/1989 | European Pat. Off. . |
| 3708060 | 9/1987 | Fed. Rep. of Germany . |
| 54-95233 | 7/1979 | Japan . |

OTHER PUBLICATIONS

Taguchi et al., CA, 92:85928f (1980).
A General Synthesis of Terminal and Internal Arylalkynes by the Palladium-Catalyzed Reaction of Alkynylzinc Reapents with Aryl Halides by Anthony O. King (List continued on next page.)

*Primary Examiner*—Nicky Chan
*Attorney, Agent, or Firm*—Gabor L. Szekeres; Martin A. Voet; Robert J. Baran

[57] ABSTRACT

Retinoid like activity is exhibited by compounds of the formula

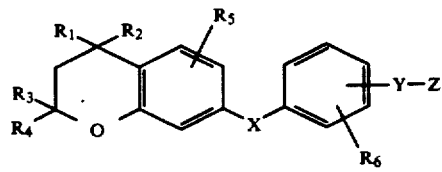

wherein the $R_1$–$R_6$ groups are independently H or straight chain or branched chain lower alkyl or cycloalkyl of 1 to 6 carbons; X symbolizes an ester or thioester linkage, Y is lower branched chain alkyl having 2 to 6 carbons, cycloalkyl having 3 to 6 carbons or is $(CH_2)_n$ where n is an integer between 0 to 6 or an alkenyl group of 2 to 6 carbons, and having 1 or 2 double bonds, or an alkynyl group of 2 to 6 carbons; and Z is H, OH, OR', OCOR', —COOH or a pharmaceutically acceptable salt, $COOR_8$, $COONR_9R_{10}$, —$CH_2OH$, $CH_2OR_{11}$, $CH_2OCOR_{11}$, CHO, $CH(OR_{12})$, $CHOR_{13}O$, —COR', $CR'(OR_{12})_2$, or $CR'OR_{13}O$; where R' is an alkyl, cycloalkyl or alkenyl group containing 1-5 carbons, $R_8$ is an alkyl group of 1-10 carbons, or a cycloalkyl group of 5-10 carbons, or $R_8$ is phenyl or lower alkylphenyl, $R_9$ and $R_{10}$ independently are hydrogen, an alkyl group of 1-10 carbons, or a cycloalkyl group of 5-10 carbons or phenyl or lower alkyl phenyl, $R_{11}$ is lower alkyl, and $R_{13}$ is a divalent alkyl radical of 2-5 carbons.

19 Claims, No Drawings

U.S. PATENT DOCUMENTS

| | | |
|---|---|---|
| 5,013,744 | 5/1991 | Chandraratna . |
| 5,015,658 | 5/1991 | Chandraratna . |
| 5,023,341 | 6/1991 | Chandraratna . |
| 5,037,825 | 8/1991 | Klaus et al. . |
| 5,045,551 | 9/1991 | Chandraratna . |
| 5,053,523 | 10/1991 | Chandraratna . |
| 5,068,252 | 11/1991 | Chandraratna . |
| 5,089,509 | 2/1992 | Chandraratna . |
| 5,130,335 | 7/1992 | Chandraratna . |
| 5,134,159 | 7/1992 | Chandraratna . |

OTHER PUBLICATIONS and Ei-ichi Negishi, *J. Org. Chem.* 43 No. 2, 1978 p. 358.
Conversion of Methyl Ketones into Terminal Acetylenes and (E)-Tri-substituted Olefins of Terpenoid Origin by Ei-ichi, Anthony O. King, and William L. Klima, *J. Org. Chem.* 45 No. 12, 1980 p. 2526.

Sporn et al., in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

Kagechika et al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'-Diacyl-1,1'-biaryls. Regiocontrolled Protection of . . . by Mervic, et al., *J. Org. Chem.*, No. 45, pp. 4720–4725, 1980.

A Dopamine Receptor and Its Application in the Design of a New Class of Rigid Pyrrolo[2,3-g]isoquinoline Antipsychotics, Gary L. Olson et al. *American Chemical Society*, 1982, vol. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356 (1982).

7-CHROMANYL ESTERS OF PHENOLS AND BENZOIC ACIDS HAVING RETINOID-LIKE ACTIVITY

CROSS-REFERENCE TO RELATED APPLICATION

The present application is a divisional of application Ser. No. 07/676,152 filed Mar. 26, 1991, which issued as U.S. Pat. No. 5,134,159 on Jul. 28, 1992.

BACKGROUND

This invention relates to novel compounds having retinoid-like activity. More specifically, the invention relates to compounds having a substituted chroman portion and a substituted phenyl portion linked to the 7-position of the chroman nucleus through an ester or thioester group.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. European Patent Application 176034A published Apr. 2, 1986 discloses tetrahydronaphthalene compounds having an ethynylbenzoic acid group. U.S. Pat. No. 4,739,098 discloses compounds of retinoid-like activity where three olefinic units from the acid-containing moiety of retinoic acid are replaced by an ethynylphenyl functionality.

The publication by Sporn et. al. in *J. Amer. Acad. Derm.* 15:756–764 (1986) discloses the compound 4-(5,5,8,8-tetramethyl-5,6,7,8-tetrahydro-2-naphthoylamino)benzoic acid as a retinoid-like agent. Further compounds of background interest to the present invention are disclosed by Shudo et al. in *Chem. Phar. Bull.* 33:404–407 (1985).

A patent application of the present inventor, assigned to the same assignee as this application, describes compounds having a substituted chroman portion and a substituted phenyl portion linked to the 6-position of the chroman nucleus through an ester or thioester group.

SUMMARY OF THE INVENTION

This invention covers compounds of Formula 1

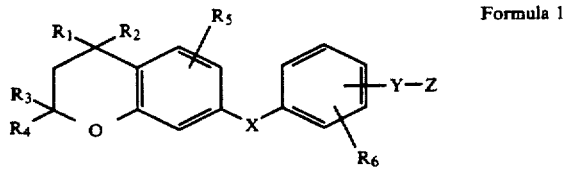

Formula 1 wherein the $R_1$–$R_6$ groups are independently H or straight chain or branched chain lower alkyl or cycloalkyl of 1 to 6 carbons; X symbolizes an ester or thioester linkage, Y is lower branched chain alkyl having 2 to 6 carbons, cycloalkyl having 3 to 6 carbons or is $(CH_2)_n$ where n is an integer between 0 to 6 or is an alkenyl group of 2 to 6 carbons and having 1 or 2 double bonds, or an alkynyl group of 2 to 6 carbons; and Z is H, OH, OR', OCOR', —COOH or a pharmaceutically acceptable salt, $COOR_8$, $COONR_9R_{10}$, —$CH_2OH$, $CH_2OR_{11}$, $CH_2OCOR_{11}$, CHO, $CH(OR_{12})$, $CHOR_{13}O$, —COR', $CR'(OR_{12})_2$, or $CR'OR_{13}O$; where R' is an alkyl, cycloalkyl or alkenyl group containing 1–5 carbons, $R_8$ is an alkyl group of 1–10 carbons, or a cycloalkyl group of 5–10 carbons, or $R_8$ is phenyl or lower alkylphenyl, $R_9$ and $R_{10}$ independently are hydrogen, an alkyl group of 1–10 carbons, or a cycloalkyl group of 5–10 carbons or phenyl or lower alkyl phenyl, $R_{11}$ is lower alkyl, $R_{12}$ is lower alkyl $R_{13}$ is divalent alkyl radical of 2–5 carbons.

In a second aspect, this invention relates to the use of the compounds of Formula 1 for treating dermatoses, such as acne, Darier's disease, psoriasis, icthyosis, eczema, atopic dermatitis and epithelial cancers. These compounds are also useful in the treatment of arthritic diseases and other immunological disorders (e.g. lupus erythematosus), in promoting wound healing, in treating dry eye syndrome and in reversing and preventing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting compounds of Formula 2 with compounds of Formula 3,

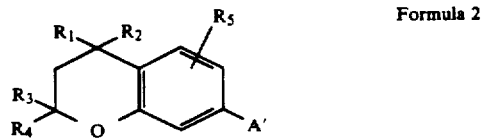

Formula 2

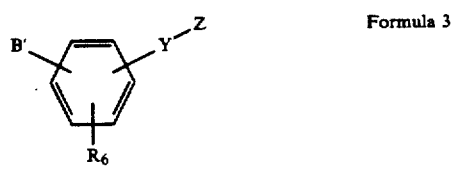

Formula 3 where $R_1$–$R_6$, Y and Z are defined as above in connection with Formula 1, and wherein one of A' and B' is an OH or SH group, and the other is a carboxylic acid (COOH) or an appropriate derivative (such as an acid chloride) suitable for forming an ester with a hydroxyl or thiol group, and where the reaction is conducted under conditions suitable for forming an ester or thioester bond between the chroman ring of the compound of Formula 2 and the phenyl ring of the compound of Formula 3.

In the process of reacting compounds of Formula 2 with the compounds of Formula 3 to form the ester or thioester linkage X of Formula 1, when Z is an alcohol or acid function it is preferred that such alcohol or acid function be protected. When, in the esterification reaction Z is an aldehyde or ketone, it may not need to be protected depending on the precise nature of the compounds and the conditions of the esterification reaction.

In still another aspect, the present invention also relates to preparation of compounds of Formula 1 by conversion of compounds having the structure of Formula 4.

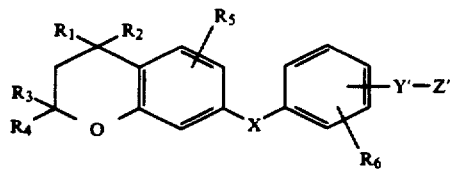

Formula 4

In Formula 4 the symbols $R_1$-$R_6$ and X are defined as above in connection with Formula 1, and Y'—Z' symbolizes such precursors of the groups Y—Z which can be readily converted by reactions well known to organic chemists, into the desired groups Y—Z. Thus, the present invention also relates to the above-noted processes involvings steps such as: converting an acid of Formula 4 to a salt; or forming an acid addition salt; converting an acid of Formula 4 to an ester; or converting an acid or ester of Formula 4 to an amide; or reducing an acid or ester of Formula 4 to an alcohol or aldehyde; or converting an alcohol of Formula 4 to an ether or exter; or oxidizing an alcohol of Formula 4 to an aidehyde; or converting an aldehyde of Formula 4 to an acetal; or converting a ketone of Formula 4 to a ketal, extending by homologation the length of the alkyl chain of a compound of Formula 4, where Y' is alkyl.

GENERAL EMBODIMENTS

Definitions

The term "ester" as used here refers to and covers any compound falling within the definition of that term as classically used in organic chemistry. The term "thioester" as used here refers to and covers any compound falling within the definition of that term as classically used in organic chemistry. With respect to the ester or thioester function symbolized by X in Formula 1 linking the chroman and phenyl moleties of the compounds of the invention, the function includes an ester or thioester derived from a phenol or thiophenol and a 7-chromanoic acid derivative (when the carbonyl group is directly attached to the chroman nucleus) and also an ester or thioester derived from a benzoic acid and 7-hydroxy-chroman or 7-thiohydroxy-chroman derivative (when the carbonyl group is directly attached to the phenyl nucleus).

Where Z (of Formula 1) is —COOH, the term "ester" covers the products derived from treatment of this function with alcohols. Where the ester is derived from compounds where Z is —CH$_2$OH, this term covers compounds of the formula —CH$_2$OOCR where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1-6 carbon atoms and includes straight as well as branched chain alkyl groups. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention are those where the X functionality of Formula 1 is COO—. In other words, preferred compounds of the invention are phenyl ester derivatives of 7-carboxy chromans.

Within the above-noted preference, still more preferred are compounds where in the Y—Z functionality of Formula 1 Y is (CH$_2$)$_n$ and n is zero, and Z is either COOH or COOR$_8$ (R$_8$ being lower alkyl, lower cycloalkyl, phenyl substituted lower alkyl, phenyl or lower alkyl substituted phenyl). In other words, still more preferred are esters of 7-carboxy chromans formed with hydroxy benzoic acids, or with hydroxy benzoic acid esters. Within this group, esters of substituted 7-carboxy chromans with 4-hydroxy benzoic acid and particularly with 4-hydroxy benzoic acid esters are still more preferred.

Even more preferred are compounds which, in addition to having the hydroxy-benzoic acid or hydroxy-benzoic acid ester residue, include substituents in the 2,2 and/or in the 4,4 and/or in the 6 position of the 7-chromanoic acid moiety. Within this group, derivatives of 2,2,4,4-tetramethyl-7-chromanoic acid are most preferred.

The most preferred specific compounds of the invention are shown in Formula 5, and are identified as follows:

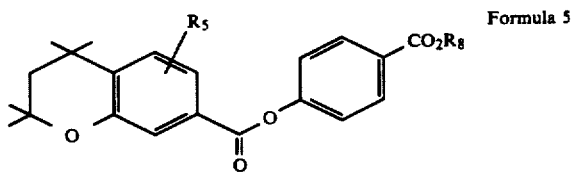

Formula 5

Ethyl 4-(2,2,4,4-tetramethyl-7-chromanoyloxy) benzoate (Compound 1, $R_5$=H and $R_8$=ethyl);
Benzyl 4-(2,2,4,4,tetramethyl-7-chromanoyloxy)benzoate (Compound 2, $R_5$=H and $R_8$=benzyl);
4-(2,2,4,4-tetramethyl-7-chromanoyloxy) benzoic acid (Compound 3, $R_5$=H and $R_8$=H);

The compounds of this invention may be administered systemically or topically, depending on such considerations as the condition to be treated, need for site-specific treatment, quantity of drug to be administered, and similar consideration In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Penna. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0,001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid like activity of these compounds was confirmed through the classic measure of retionic acid activity involving the effects of retionic acid on ornithine decarboxylase. The original work on the correlation between retinoic acid and decrease in cell proliferation was done by Verma & Boutwell, Cancer Research, 1977, 37, 2196-2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoyl-phorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in Cancer Res., 35: 1662-1670, 1975.

By way of example of retinoic acid-like activity it is noted that in the assay conducted essentially in accordance with the method of Verma & Boutwell, ibid, the following examples of the preferred compounds of the present invention (Compounds 1, 2 and 3) elicited the following percent inhibition of TPA-induced ODC activity at the given calculations:

| Compound | Dose (nmol) | % inhibition |
|---|---|---|
| 1 | 30 | 100 |
| 2 | 300 | 84 |
| 3 | 30 | 86 |

SPECIFIC EMBODIMENTS

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

The compounds of the invention, in accordance with Formula 1 are esters or thioesters containing a chroman moiety and a phenyl moiety. Accordingly, and speaking generally, the compounds of the invention can be made from the appropriate carboylic acid or derivatized carboxylic acid precursors on the one hand and thiol or alcohol precursors on the other, by synthetic methods which per se are known in the art.

Specifically, the compounds of the invention (shown in Formula 1) can be made by reaction of the precursors shown in Formula 2 and Formula 3. As is noted above, in these formulas either A' or B' is an OH or an SH group, and the other is a carboxylic acid (COOH) or a derivatized carboxylic acid (such as an acid chloride) which is capable of forming an ester or a thioester with the other group.

More specifically, and by way of example, preferred compounds of the invention comprise esters of substituted 7-carboxy chromans, i.e. esters derived from compounds of Formula 2 where A' is COOH) with hydroxybenzoic acid esters (compounds of Formula 3 where Y is $(CH_2)_n$ and n is zero, and Z is $COOR_8$, $R_8$ being an esterifying alkyl, lower alkylphenyl or phenyl group). These compounds can be prepared in accordance with Reaction Scheme 1. In this reaction the free acid, a 7-carboxychroman derivative (compound of Formula 2) is reacted with the hydroxybenzoic acid ester (compound of Formula 3) in a suitable solvent such as methylene chloride ($CH_2Cl_2$) in the presence of dicyclohexyl carbodiimide (DCC) and dimethylaminopyridine (DMAP). In Reaction Scheme 1 the symbols $R_1$ through $R_6$ have the same definition as in Formula 1.

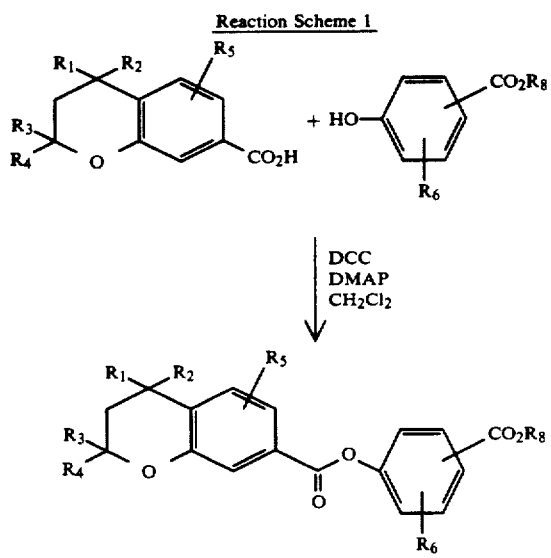

Reaction Scheme 2 shows an alternative process for synthezizing the compounds which are obtainable in Reaction Scheme 1. In accordance with this process, the substituted 7-carboxychroman derivatives are first converted to the corresponding acid chloride by treatment with a suitable reagent, for example, thionyl chloride ($SOCl_2$). The corresponding acid chloride is thereafter reacted with a hydroxybenzoic acid ester in a suitable solvent and preferably in the presence of an acid acceptor, such as triethylamine.

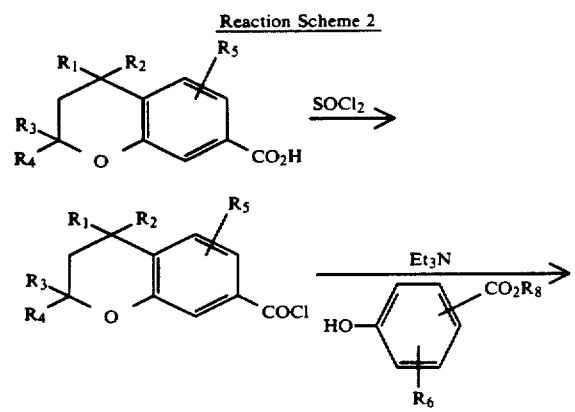

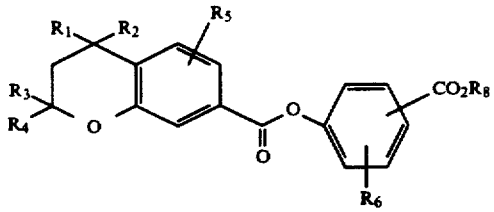

Reaction Scheme 3 shows a process for making esters of substituted 7-carboxychromans with hydroxy benzoic acid derivatives, where the desired products, (compounds of the invention) have a free carboxylic acid group. This process is similar to the condensation, in the presence of DCC and DMAP, shown in Reaction Scheme 1, except that a benzyl ester of the hydroxybenzoic acid is employed, and that in the last step of the process the benzyl ester function is selectively cleaved by hydrogenation over palladium (or other suitable catalyst), to provide the target compound having a free carboxylic acid group attached to the phenyl moiety.

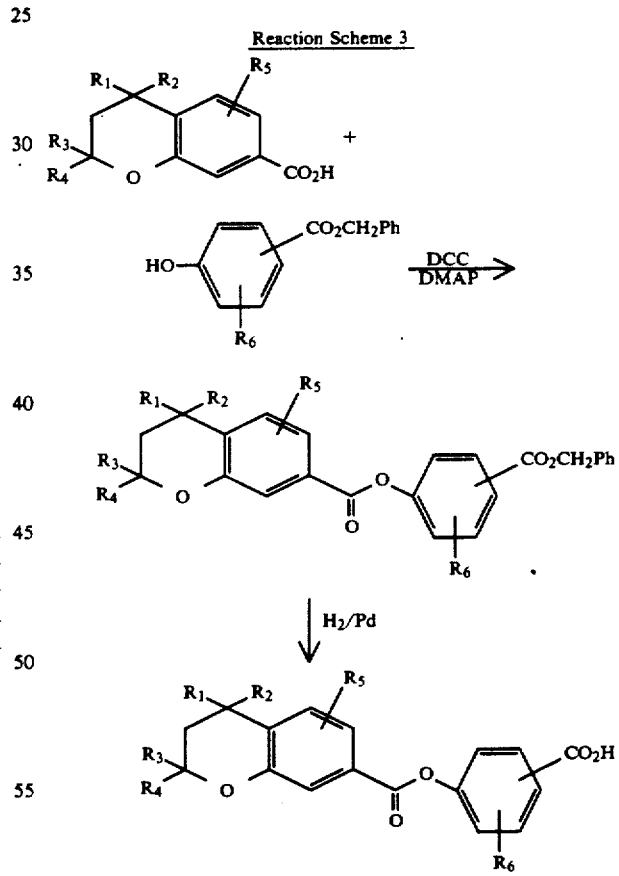

Reaction Scheme 4 shows an examplary process for the preparation of compounds of the invention derived from substituted 7-hydroxy chromans and terephtalic acid half esters, that is, compounds where, with reference to Formula 1, X is COO with the carbonyl group attached to the phenyl moiety, Y is $(CH_2)_n$ and n is zero. The condensation shown in this reaction is performed in the presence of DCC and DMAP. It should be understood however, that several variations of this process are possible, for example the terephtalic acid half ester can be converted into an acid chloride (or some other activated derivative of the carboxylic acid) and the acid chloride (or other active derivative) can be reacted with the 7-hydroxy-chroman derivative in a suitable solvent and in the presence of an acid acceptor, in analogy to the reaction sequence shown in Reaction Scheme 2. Utilizing the benzyl half ester of terephtalic acid (or of a substituted terephtalic acid) in analogy with Reaction Scheme 3, permits selective cleavage of the benzyl ester function by hydrogenation, and synthesis of the corresponding 7-hydroxy-chroman derivative esterified with terephatalic acid and bearing, attached to the phenyl, group a free carboxylic acid function.

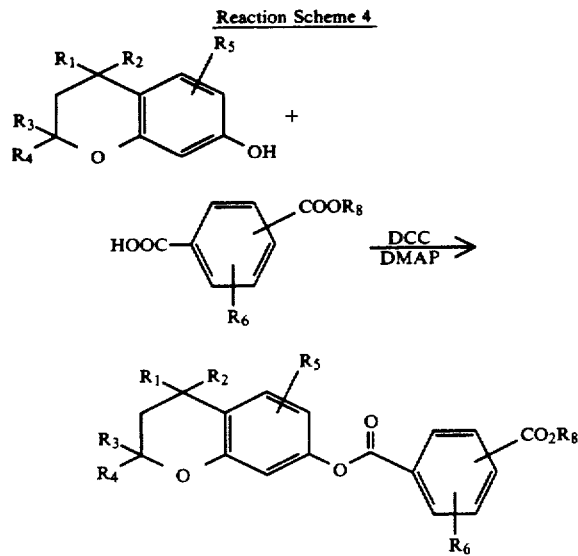

Reaction Scheme 4

The synthetic procedures outlined in an examplary manner in connection with Reaction Schemes 1–4, can also be adapted for the preparation of the thioester compounds of the present invention.

As is noted above in connection with Formula 4, compounds of the invention (Formula 1) may also be prepared by performing certain synthetic steps on compounds which are either already embraced by Formula 1, or are such precursors shown in Formula 4, which readily lend themselves to synthetic steps leading to compounds of the invention. In this regard free carboxylic acids of Formula 4, that is compounds possessing the "chroman to phenyl" ester linkage but having a free or appropriately protected carboxylic group on the phenyl moiety, can be converted to salts, esterified, converted to an amide, reduced to an aldehyde or an alcohol. The corresponding alcohols and aldehydes can be esterified or converted to acetals, as applicable. Alternatively the carbon chain of Y—Z of Formula 1 may be subjected to chain elongation by homologation. As it will be recognized by those skilled in synthetic organic chemistry, the foregoing conversions can be performed by adapting generally known synthetic procedures to the compounds of the invention. In performing some of the above-noted synthetic steps on compounds of Formula 1 or of Formula 4, care may need to be exercised not to saponify or otherwise destroy the ester linkage between the chroman and phenyl moieties.

The compounds of Formula 3 which comprise starting materials or intermediates to the compounds of the present invention, are either available commercially, or are readily synthesized by known synthetic methods within the skill of ordinary artisan in the field. For example, 4-hydroxy benzoic acid is commercially available, and can be esterified to provide, for example, ethyl 4-hydroxy benzoate which is an important intermediate for the synthesis of certain specific examples of the compounds of the present invention. The mono ethyl ester of terephtalic acid, another intermediate in accordance with Formula 3, is also available commercially or is readily synthesized by known methods.

Intermediates of Formula 2 where A' is COOH, can be synthesized by the reaction sequences described below.

Specifically, compounds of Formula 2 where $R_3$ and $R_4$ are hydrogen, and A' is COOH are synthesized according to Reaction Scheme 5.

Reaction Scheme 5

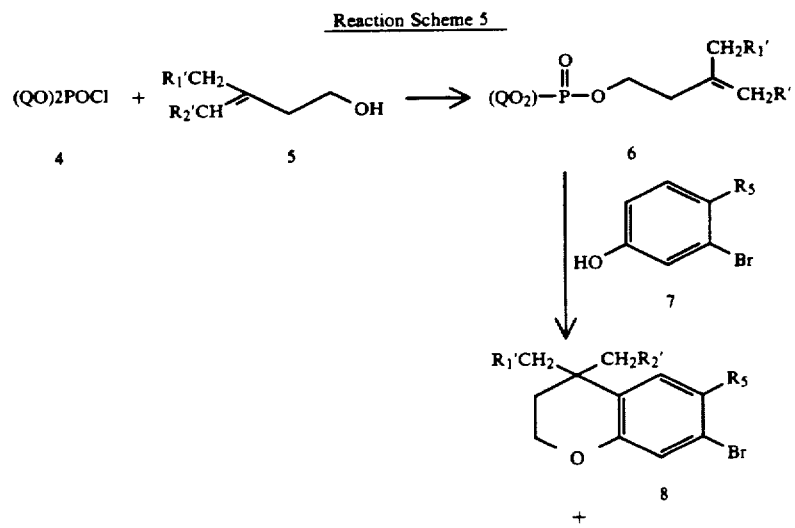

Reaction Scheme 5

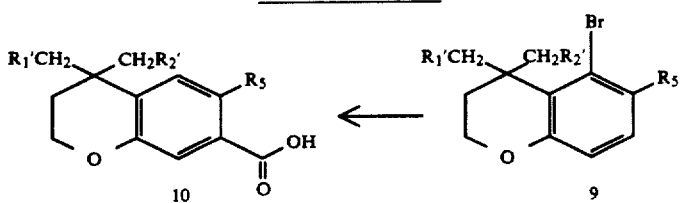

In Reaction Scheme 5 Q is phenyl and $R_1'$, $R_2''$ and $R_5$ are hydrogen or lower alkyl having 1 to 5 carbons. The reaction sequence is hereinafter further described generally but with emphasis to the preferred case where $R'_1$ and $R_2'$ both are hydrogen, i.e. for the synthesis of a 4,4-dimethyl-7-carboxy chroman (Compound 10). The phosphate (Compound 6) is prepared from the corresponding diphenyl chlorophosphate (Compound 4) and 3-methyl-3-butene-1-ol (Compound 5, $R_1'$ and $R_2'$ are both H) which is available from Aldrich, Chemical Company, or is prepared by means known in the art. It is preferred to prepare Compound 6 by dissolving the alcohol (Compound 5) in about a 10% excess of pyridine (or like solvent) under an inert atmosphere cooled to approximately −10 degrees C. This solution is then added drop-wise, under an inert atmosphere, to a solution of diphenyl chlorophospate (Compound 4), in about an equal amount of reaction solvent. About a 2-5% molar excess of diphenyl chlorophosphate (Compound 4) relative to the alcohol (Compound 5) is employed. The mixture is heated at reflux for 1 to 5 hours, preferably about 3, to affect the reaction. The product is then recovered by conventional means. The diphenyl phosphate ester (Compound 6) is then reacted with the 3-bromo phenol derivative (Compound 7) to affect formation of an isomeric mixture of chromans (Compound 8 and Compound 9). For example, 3-bromo-phenol (Compound 7, $R_5$=H) is added to a flask already containing stannic chloride under argon which has been cooled to −10 degrees to 10 degrees C. After thorough mixing of this combination for about 15 minutes to an hour at the reduced temperature, the phosphate (Compound 6) is added. When the addition of the phosphate (Compound 6) is completed, the mixture is stirred at about ambient temperature for up to 24 hours. Then the reaction is quenched with a dilute solution of aqueous alkali metal base or the like. The isomeric mixture is then separated by conventional means to give the desired 7-bromo-chroman (Compound 8).

Alternatively, the desired 7-substituted chromans can be separated from their potential regio-isomeric impurities at the carboxylic acid stage or at the final coupling stage.

The carboxylic acid function is then introduced into the 7-position of the 4,4-disubstituted bromochroman by metal halogen exchange. The bromochroman (Compound 8) is treated with tertbutyl-lithium (or other appropriate metal halogen exchange reagents) followed by carbon dioxide quench. Subsequent acidification gives the 4,4-dialkyl-7-carboxy chroman derivative which contains the desired $R_1'$, $R_2'$, $R_3$, $R_4$ and $R_5$ substituents (Compound 10).

Reaction Scheme 6 illustrates an alternative method for preparing compounds of Formula 2 where $R_1$–$R_5$ are as previously described in Reaction Scheme 5.

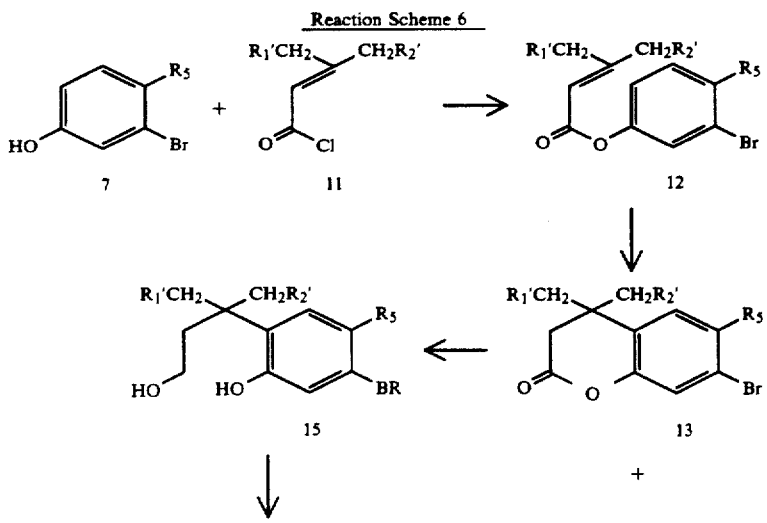

Reaction Scheme 6

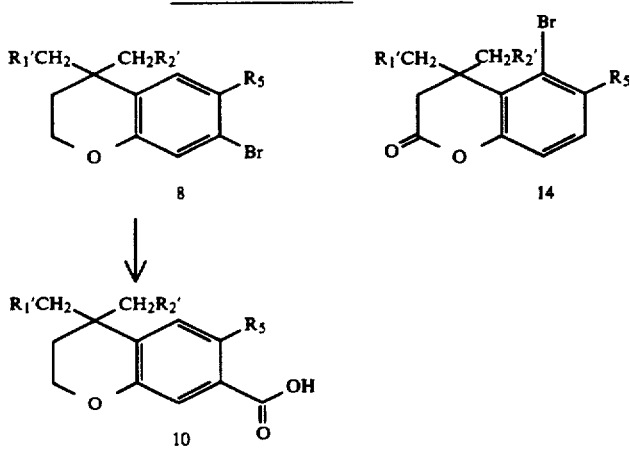

Thus, in accordance with Reaction Scheme 6, 3-bromo phenol, or a 3-bromo phenol substituted in the 4 (para) position by an alkyl substituent (Compound 7) is acylated with an acylating agent, such as the acid chloride (Compound 11) derived from 3,3-dimethylacrylic acid or from another appropriately substituted acrylic acid ($R_1'$ and $R_2'$ is either H or lower alkyl). The acylation of the 3-bromo-phenol (Compound 7) with the acid chloride (Compound 11) is preferably conducted in the presence of a strong base (e.g. sodium hydride) in an inert solvent (such as tetrahydrofuran). The resulting phenyl-acrylate (Compound 12) is ring closed under Friedel-Crafts type reaction conditions (e.g. $AlCl_3$ catalyst, in an inert solvent such as methylene chloride) to provide two positional isomers (Compound 13) and (Compound 14) of the 2-oxo-chroman derivative, each of which bears, in the 4-position, the $CH_2R_1'$ and $CH_2R_2'$ substituents and where $R_5$ is hydrogen or lower alkyl. As described previously for Reaction Scheme 5, the mixture is then separated by conventional means to obtain the desired 7-bromo-2-oxo-chroman (Compound 13). It should be noted that as also described previously in connection with Reaction Scheme 5 the 7-bromo-2-oxo chroman (Compound 13) can be separated from the potential regio-isomeric impurities at the carboxylic acid stage or at the final coupling stage. The 2-oxo-7-bromo-chroman (Compound 13) is thereafter reduced with lithium aluminum hydride or an appropriate reducing agent to provide the 7-bromo-diol (Compound 15). The diol (Compound 15) is then mono-mesylated at the primary alcohol position followed by intramolecular nucleophilic displacement of a mesyl leaving group, to give the 7-bromo-chroman (Compound 8) which bears the desired $CH_2-R_1'$, $CH_2R_2'$ and $R_5$ substituents. The carboxylic acid function is introduced into the 7-position in the same manner as described previously in Reaction Scheme 5 to give the 7-carboxy chroman (Compound 10).

The intermediate chroman derivatives of Formula 2 where $R_1-R_4$ are lower alkyl, $R_5$ is H or lower alkyl, and A' is COOH may be prepared in accordance with the synthetic steps illustrated in Reaction Scheme 7.

Reaction Scheme 7

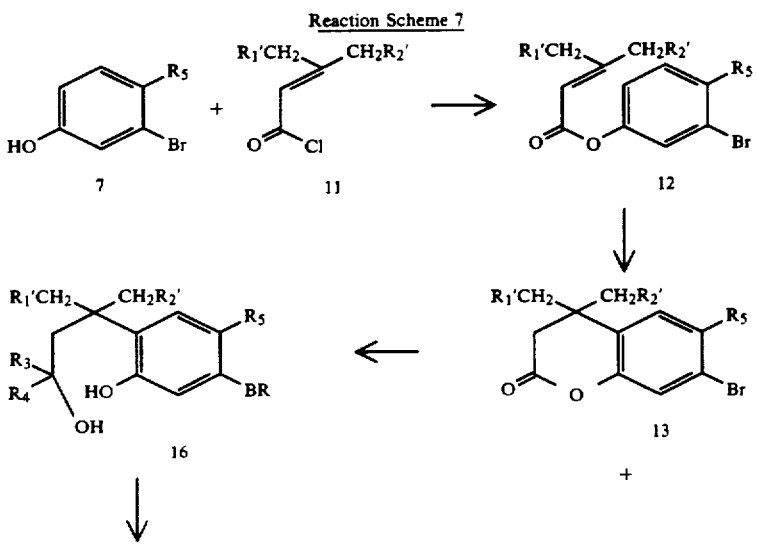

Reaction Scheme 7 —continued

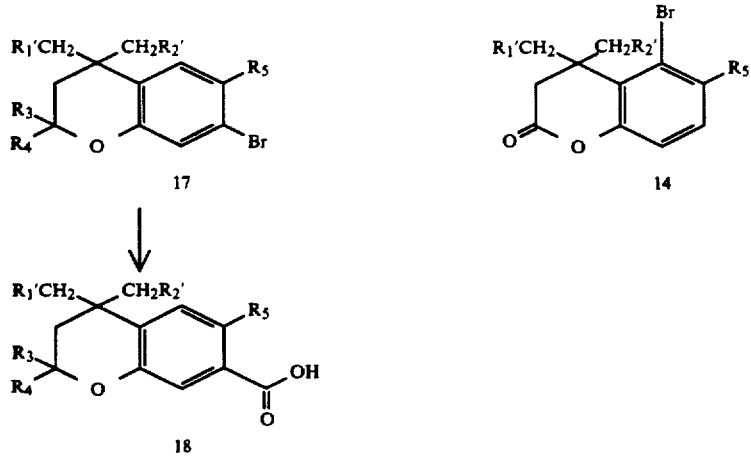

With reference to Reaction Scheme 7, the 3-bromophenol derivative, where $R_5$ is hydrogen or lower alkyl, (Compound 7) is acylated with an acylating agent, such as acid chloride (Compound 11) derived from 3,3-dimethyl acrylic acid or from another appropriately substituted acrylic acid. ($R_1'$ and $R_2'$ are hydrogen or lower alkyl). As previously described cyclization of Compound 12 under Friedel-Crafts type reaction conditions results in the formation of positional isomers, (Compounds 13 and 14), where the bromo substituent of the meta (3) position of the phenol Compound 7 becomes, in the target chroman compounds the substituent either at the 5-position or the 7-position of the chroman nucleus. Thus, with specific reference to Reaction Scheme 7, the acylation of the bromo phenol (Compound 7) with the acid chloride (Compound 11) is preferably conducted in the presence of a strong base in an inert solvent, analogus to the conditions described for Reaction Scheme 6. The phenyl-acrylate (Compound 12) is ring closed under Friedel Craftes type reaction conditions as described for Reaction Scheme 6 to provide a mixture of two isomers. (Compound 13 and Compound 14) each of which bears, in the 4-position, the $CH_2R_1$ and $CH_2R_2$ substituents. The isomers are then separated as described previously for Reaction Schemes 5 and 6. The 2-oxo-7-bromo derivative (Compound 13) is thereafter treated with a Grignard reagent to introduce the $R_3$ and $R_4$ substituents. In the preferred embodiments, $R_3$ and $R_4$ are identical, for example both are methyl or ethyl. When $R_3$ and $R_4$ are methyl, the Grignard reagent is preferably methylmagnesium chloride (dissolved in tetrahydrofuran). To carry out the Grignard reaction a solution of Compound 13 in a suitable solvent (for example in dry diethylether) is added to this Grignard reagent. The resulting tertiary phenol that has undergone ring opening is shown as Compound 16 in Reaction Scheme 7.

Compound 16 which already has the desired $R_1$, $R_2$, $R_3$, $R_4$ and $R_5$ substituents, is ring closed under acidic conditions, (e.g. by heating in aqueous sulfuric acid) to provide the chroman derivative (Compound 17). The carboxylic acid moiety is introduced by metal halogen exchange followed by reaction with carbon dioxide, as described previously, to give the desired 7-carboxy chroman (Compound 18).

Reaction Scheme 8

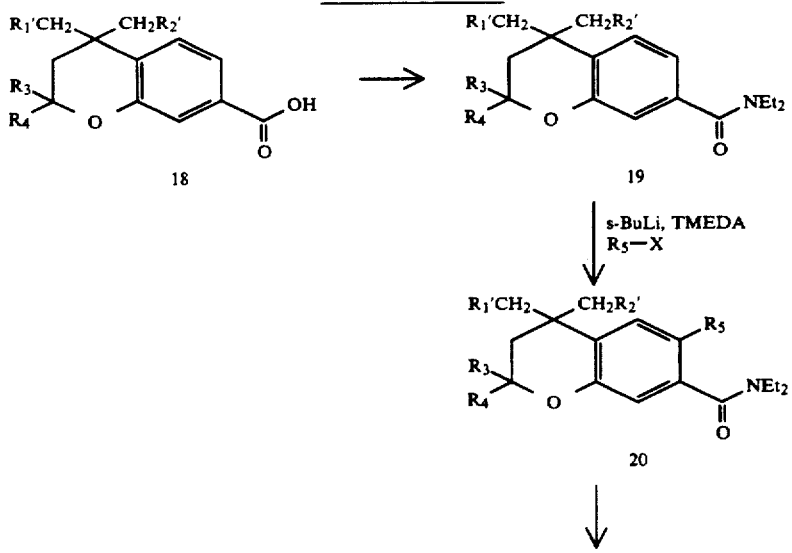

Reaction Scheme 8

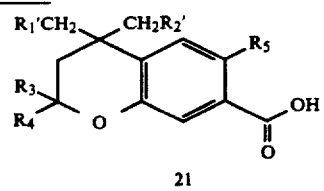

An alternative route for synthesizing compounds of Formula 2 where $R_3$ and $R_4$ are hydrogen or lower alkyl, $R_5$ is lower alkyl and $A'$ is COOH, is shown in Reaction Scheme 8. This scheme serves as an illustrative example for the synthesis of compounds of the invention having substituents in the 4,4 and 6 positions or in the 2,2,4,4 and 6 positions of the chroman nucleus. In this scheme, the 7-carboxy-chromans (Compound 18) where $R_3$ and $R_4$ are hydrogen or lower alkyl serve as starting materials. Compound 18 is obtained in accordance with Reaction Scheme 5, 6 when $R_3$ and $R_4$=H and in accordance with Reaction Scheme 7 (when $R_3$ and $R_4$=CH$_3$). Compound 18 is converted to the corresponding acid chloride, and thereafter to the corresponding diethylamide (Compound 19) through treatment with thionyl chloride and subsequently by treatment with diethylamine. The lower alkyl substituent at the 6 position of the chroman nucleus is introduced by alkylation of Compound 19 with an alkyl halide ($R_5$—X), after treating Compound 19 with secondary butyl lithium in tetramethylethylenediamine (TMEDA). The resulting 6-substituted diethylamide (Compound 20) is thereafter converted into the corresponding 4,4,6 substituted or 2,2,4,4,6 substituted 7-carboxy chroman (Compound 21) by hydrolysis, for example under appropriate acidic or basic conditions.

shown in Reaction Scheme 9. The 7-bromo-2-oxo-chroman, also known as dihydrocoumarin (Compound 22) can be obtained, for example, by the steps outlined in Reaction Scheme 7 using acrylic acid chloride ($R_1$, $R_2$=H in Compound 11) and 3-bromo phenol derivative ($R_5$=H or lower alkyl in Compound 7). Dihydro coumarin (Compound 22) is subjected to the reaction sequence outlined in Reaction Scheme 9 to yield, through the intermediate compounds 23 and 24, the 2,2 disubstituted 7-carboxychroman (Compound 25). Compound 25 then can be reacted with an appropriate compound of Formula 3 to provide the esters of the invention, in accordance with Formula 1. Alternatively, the 2,2 disubstituted 7-carboxy chroman (Compound 25) where $R_5$ is hydrogen may be alkylated in the 6- position of the chroman nucleus in accordance with the synthetic sequence described above in Reaction Scheme 8 in connection with the analogous alkylation of 4,4 disubstituted and 2,2,4,4 tetrasubstituted 7-carboxy chromans (Compound 18). Thus, with specific reference now to Reaction Scheme 10, Compound 26 is first converted to the corresponding diethylamide (Compound 27). The diethylamide (Compound 27) is alkylated with an alkyl halide ($R_5$X) in the presence of secondary butyl lithium in tetramethylethylene diamine. The resulting 6-substituted diethylamide (Com-

Reaction Scheme 9

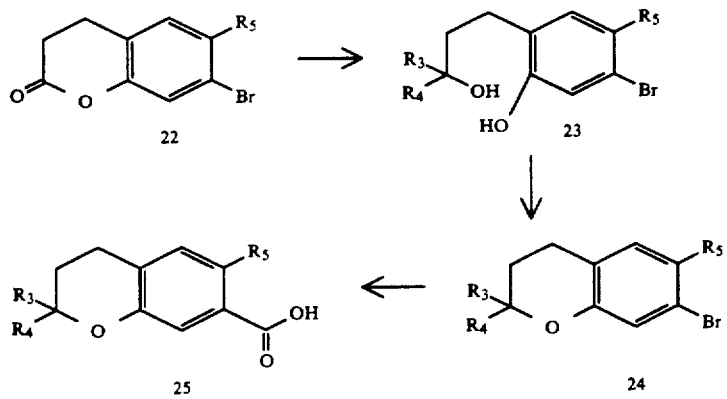

The synthetic sequence which provides 7-carboxy-chroman intermediates unsubstituted in the 4 position, and substitutee or unsubstituted in the 6-position, is pound 28) is thereafter converted into the corresponding 2,2,6-substituted 7-carboxy chroman (Compound 29) for example by hydrolysis with base or acid.

Reaction Scheme 10

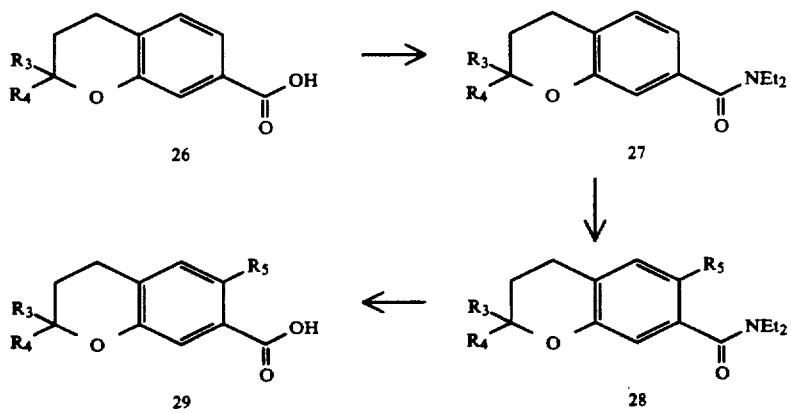

It should be noted that in accordance with Formula 2 the $R_5$ substituent may be attached to the 6-position, which has been described and is preferred, but also to the 5 position or 8-position of the chroman nucleus.

In addition, although the bromo substituted phenols are described and preferred, the iodo, chloro and other appropriately halogenated phenols can also be used in the above described synthetic steps leading to the compounds of the present invention.

The following examples of specific compounds of the invention, and specific examples of the synthetic steps in which the compounds and certain intermediates are made, are set out to illustrate the invention, not to limit its scope.

SPECIFIC EXAMPLES

5-Bromophenyl 3,3-dimethyl acrylate (Compound 30)

To an ice-cooled suspension of 4 g (100 mmol) of sodium hydride (60% in mineral oil) in 50 ml of dry THF was added dropwise a solution of 15.7 g( 90.7 mmol) of 3-bromo phenol in 25 ml of dry THF. The mixture was stirred at 0 degrees C. for 0.5 hours and then treated with a solution of 10.65 g (90.0 mmol) of dimethyl acryloyl chloride in 30 ml of dry THF. The mixture was allowed to warm to room temperature and stirred for 24 hours. The reaction mixture was poured onto 200 ml of ice water containing 3 ml of glacial acetic acid. The mixture was extracted with 2×250 ml ether and the combined ether extracts were washed with 200 ml of water and 100 ml saturated NaCl solution and dried (MgSO$_4$). The solvent was removed in vacuo and the residue purified by kugelrohr distillation to give the title compound as a clear oil.

PMR (CDCl$_3$): & 2.02 (3H, s), 2.28 (3H, s), 5.94 (1H, broad s), 7.06–7.12 (1H, m ), 7.28 (1H, t, J~8.0 Hz), 7.34 (1H, t, J~2.0 Hz), 7.37–7.42 (1H, m).

3-Bromo-2-(1,1,3-trimethyl-3-hydroxybutyl)phenol (Compound 32)

To a stirred, ice-cooled suspension of 21 g (158 mmol) of aluminum chloride in 200 ml of methylene chloride was added slowly a solution of 23.74 g (93.1 mmol) of 5-bromophenyl-3,3-dimethyl acrylate (Compound 30) in 100 ml of methylene chloride. The mixture was warmed to room temperature and stirred for 52 hours. The mixture was poured into a mixture of ice and brine and the organic layer was separated. The aqueous layer was extracted with 2×100 ml ether. The organic extracts were combined and washed with 2×250 ml of water and 50 ml of saturated NaCl solution and dried (MgSO$_4$). The solvent was removed in vacuo and the residue was partially purified by flash column chromatography, (silica; 5% ethyl acetate/hexane) to give impure 4,4-dimethyl-7-bromo-2-oxochroman (Compound 31) as a yellow oil which was used in the next step without further purification. To an ice-cooled solution of 10 g of this impure 4,4,dimethyl-7-bromo-2-oxo-chroman (Compound 31) in 200 ml of dry THF was added under argon 39.2 ml of 3.0M Methyl Magnesium Chloride (117.6 mmol) in THF. The reaction mixture was allowed warm to room temperature and stirred for 5 hours. The reaction mixture was then poured into ice water containing 2 ml of sulfuric acid and the organic layer was separated. The aqueous layer was extracted with 200 ml of ether. The organic extracts were combined and washed with 200 ml of water and 200 ml of brine and dried (MgSO$_4$). The solvent was removed in vacuo and the residue purified by flash column chromatography (silica; 10% ethylacetate/hexanes) to give the title compound as a pale yellow oil.

PMR (CDCl$_3$): & 0.98 (6H, s), 1.36 (6H, s), 2.15 (2H, s), 6.82 (1H, d, J~1.9 Hz), 6.86 (1H, dd, J~8.3 Hz, 1.9 Hz), 7.04 (1H, d, J~8.3 Hz) .

2,2,4,4-tetramethyl-7-bromochroman (Compound 33)

A mixture of 5.42 (18.9 mmol) of 3-bromo-2(1,1,3 trimethyl-3-hydroxy-butyl) phenol (Compound 32) and 50 ml of 20 percent aqueous sulfuric acid was heated at reflux for 24 hours. The reaction mixture was cooled to room temperature and treated with 100 ml of ether. The organic layer was separated and the aqueous layer was extracted with 50 ml of ether. The ether extracts were combined and washed with 100 ml of water and 100 ml saturated NaCl solution and dried (MgSO$_4$). The solvent was removed in vacuo and the residue was purified by Kugelrohr distillation to give the impure title compound as a pale yellow oil.

PMR (CDCl$_3$): & 1.22 (6H, s), 1.24 (6H, s), 1.72 (2H, s), 6.87 (1H, d, J~2.0 Hz), 6.92 (1H, dd, J~8.3 Hz, 2.0 Hz), 7.02 (1H, d, J~8.3 Hz).

2,2,4,4-Tetramethyl-7-carboxychroman (Compound 34)

A solution of 1.78 g (6.6 mmol) of 2,2,4,4-Tetramethyl-7-bromochroman (Compound 33) in 10 ml of ether was cooled to −78 degrees C. under Argon and treated dropwise with 7.76 ml (13.19 mmol) of 1.7M t-Butyl Lithium solution. The mixture was stirred at −78 degrees C. for 5 hours. A rapid stream of carbon dioxide gas was then bubbled through the mixture for 1 hour while warming to room temperature. The mixture was then taken up with water and ether and the layers were separated. The ether layer was extracted with water and the combined aqueous extracts were washed with ether and then acidified with 1N HCl until a white precipitate formed. The acidified mixture was cooled overnight and then extracted with ether. The organic layer was then washed with water and with saturated sodium chloride solution and dried (MgSO₄). The solvent was removed in vacuo to give the title compound as a white solid.

PMR (CDCl₃): & 1.36 (6H, s), 1.38 (6H, s), 1.87 (2H, s), 7.38 (1H, d, J~1.8 Hz), 7.56 (1H, d J~1.8 Hz) 7.65 (1H, dd, J~8.1 Hz, 1.8 Hz).

Ethyl-4-(2,2,4,4-Tetramethyl-7-chromanoyl-oxy)benzoate (Compound 1)

A solution of 450 mg (1.923 mmol) of 2,2,4,4-Tetramethyl-7-carboxychroman (Compound 34) and 320 mg (1,926 mmol) of Ethyl-4-hydroxy benzoate in 15 ml of methylene chloride was treated sequentially with 397 mg (1,924 mmol) of Dicyclohexylcarbodiimide and 58 mg (0.475 mmol) of 4-Dimethyl-aminopyridine. The mixture was stirred for 18 hours and then filtered. The filtrate was concentrated in-vacuo and the resulting residue was purified flash chromatography (silica: 10% ethyl acetate in hexanes) to give the title compound as a white solid.

PMR (CDCl₃): & 1.34-1.45 (15 H, m), 4.39 (2H, q, J~7.0 Hz), 7.28 (2H, a, J~8.7 Hz), 7.42 (1H, d, J~8.2 Hz), 7.65 (1H, d, J~1.8 Hz), 7.73 (1H, dd, J~8.2 Hz, 1.8 Hz), 8.12 (2H, d, J~8.7 Hz).

Benzyl-4(2,2,4,4-tetramethyl-7-chromanoyloxy)benzoate (Compound 2)

A solution of 450 mg (1,923 mmol) of 2,2,4,4 Tetramethyl-7-carboxychroman (Compound 34) and 440 mg (1,930) of Benzyl-4-hydroxy benzoate in 15 ml of methylene chloride was treated sequentially with 400 mg (1.940) of 1,3-Dicyclohexyilcarbodiimide and 58 mg (0.475 mmol) of Dimethylaminopyridine. The mixture was stirred for 18 hours and filtered. The filtrate was concentrated in-vacuo and the residue was purified by flash chromatography (silica; 10% ethylacetate in hexanes) to give the title compound as a white solid.

PMR (CDCl₃): & 1.39 (6H, s), 1.40 (6H, s), 1.89 (2H, s), 5.38 (2H, s), 7.29 (2H, d, J~8.3 Hz), 7.34–7.49 (6H, m), 7.66 (1H, d, J~1.8 Hz), 7.73 (1H, dd, J~8.1 Hz, 1.8 Hz), 8.16 (2H, d, J~8.3 Hz).

By substituting, for example, methyl or propyl 4-hydroxybenzoate for benzyl 4-hydroxybenzoate or for ethyl 4-hydroxybenzoate as in the immediately preceding two specific examples, methyl 4-(2,2,4,4,tetramethyl-7-chromanoyloxy benzoate and propyl 4-(2,2,4,4-tetramethyl-7-chromanoyloxy) benzoate can be obtained, respectively.

4-(2,2,4,4-tetramethyl-7-chromanoyloxy) benzoic acid (Compound 3)

To a degassed solution of 400 mg (0.9 mmol) of Benzyl 4-(2,2,4,4-tetramethyl-7-chromanoyloxy) benzoate (Compound 2) in 15 ml of Ethylacetate, under argon was added 130 mg of 10% Palladium on carbon. The mixture was placed under a hydrogen atmosphere at 5 PSI and hydrogenated for 3 hours. The mixture was then filtered through celite and the filtrate was concentrated in-vacuo to give the title compound as a white solid.

PMR (CDCl₃): & 1.39 (6H, s), 1.40 (6H, s), 1.90 (2H, s), 7.34 (2H, d, J~8.7 Hz), 7.43 (1H, d, J~8.1 Hz), 7.67 (1H, d, J~1.6 Hz), 7.74 (1H, dd, J~8.1 Hz, 1.6 Hz), 8.21 (2H, d, J~8.7 Hz).

What is claimed is:

1. A compounds of the formula

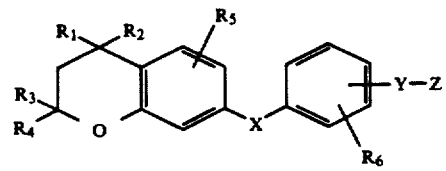

wherein
the $R_1$–$R_6$ groups are independently H or straight chain or branched chain lower alkyl or cycloalkyl groups of up to 6 carbons;

X is —OOC— or —SOC—;

Y is cycloalkyl or branched chain alkyl group of 3 to 6 carbons, or is $(CH_2)_n$ where n is an integer between 0 to 6, and Z is OH, OR', OCOR', —COOH or a pharmaceutically acceptable salt, COOR₈, CONR₉R₁₀, —CH₂OH, CH₂OR₁₁, CH₂OCOR₁₁, CHO, CH(OR₁₂)₂, CHOR₁₃O, —COR', CR'(OR₁₂)₂, or CR'OR₁₃O where R' is an alkyl, cycloalkyl or alkenyl group containing up to 5 carbons, R₈ is an alkyl group of 1-10 carbons, or a cycloalkyl group of 5-10 carbons, or R₈ is phenyl or lower alkylphenyl, R₉ and R₁₀ independently are hydrogen, an alkyl group of 1-10 carbons, or a cycloalkyl group of 5-10 carbons or phenyl or lower alkyl phenyl, R₁₁ is lower alkyl, R₁₂ is lower alkyl and R₁₃ is divalent alkyl radical of 2 to 5 carbons.

2. A compound of claim 1 where Y is $(CH_2)_n$ and n is zero.

3. A compound of claim 2 where Z is COOR₈, wherein R₈, is H₇, or lower alkyl.

4. A compound of claim 1 wherein R₁ and R₂ are methyl, R₃, R₄ and R₅ are hydrogen.

5. A compound of claim 1 wherein R₅ is attached to the 6-position of the chroman nucleus.

6. A compound of claim 1 wherein R₃ and R₄ are methyl, R₁ R₂ and R₅ are hydrogen.

7. A compound of claim 1 wherein R₁, R₂, R₃, and R₄ all are methyl.

8. A compound of claim 7 wherein R₅ is attached to the 6-position of the chroman nucleus.

9. A compound of claim 1 where X is —OOC.

10. A compound of claim 1 where X is —SOC.

11. A pharmaceutical composition comprising one or more compounds set forth in claim 1 and a pharmaceutically acceptable excipient.

12. A compound of the formula

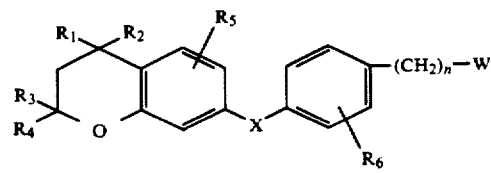

wherein the $R_1$-$R_6$ groups are independently H or straight chain or branched chain lower alkyl or cycloalkyl groups of up to 6 carbons;

X is —OOC— or —SOC—;

n is an integer between 0 to 6;

W is COOR$_{8'}$ and R$_{8'}$ is H, or lower alkyl, or W is CONR$_9$R$_{10}$ where R$_9$ and R$_{10}$ independently are H or lower alkyl or phenyl.

13. A compound of claim 12 wherein n is zero.

14. A compound of claim 12 wherein $R_1$-$R_4$ groups are independently H or CH$_3$.

15. A pharmaceutical composition comprising one or more compounds set forth in claim 12 and a pharmaceutically acceptable excipient.

16. A compound of the formula

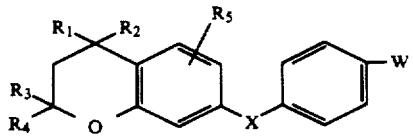

wherein $R_1$-$R_4$ are independently H or CH$_3$, R$_5$ is H or lower alkyl of 1-6 carbons;

X is —OOC— or —SOC—;

W is COOR$_{8''}$ and R$_{8''}$ is H, lower alkyl, phenyl or benzyl, or W is CONR$_9$R$_{10}$ independently are H or lower alkyl, or a pharmaceutically acceptable salt thereof.

17. A compound of claim 16 wherein $R_1$-$R_4$ all are methyl.

18. A compound of claim 17 wherein R$_5$ is H or methyl and R$_{8''}$ is H or lower alkyl, or pharmaceutically acceptable salt of the compounds where R$_{8''}$ is H.

19. A compound of claim 18 wherein R$_5$ is H.

* * * * *

UNITED STATES PATENT AND TRADEMARK OFFICE
CERTIFICATE OF CORRECTION

PATENT NO.  : 5,324,744

DATED       : June 28, 1994

INVENTOR(S) : Roshantha A. S. Chandraratna

It is certified that error appears in the above-identified patent and that said Letters Patent is hereby corrected as shown below:

Column 3, line 20, "aide-" should be --alde--;

Column 3, line 22, "exter" should be --ester--;

Column 3, line 23, "aidehyde" should be --aldehyde--;

Column 4, line 13, after "for" add --any--;

Column 6, line 57, "carboylic" should be --carboxylic--;

Column 17, line 68, "substitutee" should be --substituted--;

Column 21, line 23, " 1,926" should be --1.926--;

Column 21, line 25, "1,924" should be --1.924--;

Column 21, line 39, "1,923" should be --1.923--;

Column 21, line 41, "1,930" should be --1.930--;

Column 21, line 29, before "flash" add --by--;

Column 22, line 43, "$H_7$" should be --H--;

Column 24, line 13, before "independently" add --where $R_9$ and $R_{10}$--.

UNITED STATES PATENT AND TRADEMARK OFFICE
CERTIFICATE OF CORRECTION

PATENT NO. : 5,324,744

DATED : June 28, 1994

INVENTOR(S) : Roshantha A.S. Chandraratna

It is certified that error appears in the above-identified patent and that said Letters Patent is hereby corrected as shown below:

Column 4, line 40, "COO" should be --COO--;

Column 7, line 4, "COOH)" should be --(COOH)--;

Column 12, <u>Reaction Scheme 6</u>, "BR" should be --Br--;

Column 14, <u>Reaction Scheme 7</u>, "BR" should be --Br--.

Signed and Sealed this

Sixteenth Day of May, 1995

*Attest:*

BRUCE LEHMAN

*Attesting Officer*      *Commissioner of Patents and Trademarks*